US009360687B2

(12) United States Patent
Yaacobi

(10) Patent No.: US 9,360,687 B2
(45) Date of Patent: Jun. 7, 2016

(54) CONTACT LENS CLEANING SYSTEMS

(71) Applicant: Yoseph Yaacobi, Fort Worth, TX (US)

(72) Inventor: Yoseph Yaacobi, Fort Worth, TX (US)

(*) Notice: Subject to any disclaimer, the term of this patent is extended or adjusted under 35 U.S.C. 154(b) by 0 days.

(21) Appl. No.: 14/345,422

(22) PCT Filed: Oct. 12, 2012

(86) PCT No.: PCT/US2012/060119
§ 371 (c)(1),
(2) Date: Mar. 18, 2014

(87) PCT Pub. No.: WO2013/056165
PCT Pub. Date: Apr. 18, 2013

(65) Prior Publication Data
US 2014/0366917 A1 Dec. 18, 2014

Related U.S. Application Data

(60) Provisional application No. 61/546,284, filed on Oct. 12, 2011.

(51) Int. Cl.
A61L 12/12 (2006.01)
G02C 13/00 (2006.01)

(52) U.S. Cl.
CPC ............ G02C 13/008 (2013.01); A61L 12/128 (2013.01); A61L 2202/14 (2013.01)

(58) Field of Classification Search
CPC .................................................. A61L 12/086
USPC ........................................................ 422/28
See application file for complete search history.

(56) References Cited

U.S. PATENT DOCUMENTS

| 4,776,360 A | 10/1988 | Ching Shih |
| 4,816,232 A | 3/1989 | Barrau et al. |
| 4,852,591 A | 8/1989 | Wisotzki et al. |
| 4,852,592 A * | 8/1989 | DiGangi et al. ............ 134/57 R |
| 4,971,765 A * | 11/1990 | Loretti et al. ................ 422/116 |
| 4,986,290 A | 1/1991 | Oguma et al. |

(Continued)

FOREIGN PATENT DOCUMENTS

| GB | 1484945 A | 9/1977 |
| WO | 95/34327 | 12/1995 |

OTHER PUBLICATIONS

International Search Report issued by the IPEA/US in the corresponding PCT application PCT/US12/060119 dated Jan. 18, 2013.

(Continued)

Primary Examiner — Sean E Conley
Assistant Examiner — Donald Spamer

(57) ABSTRACT

A cleaning system configured to use a hydrogen peroxide solution to clean contact lenses. The cleaning system includes a reservoir to hold the cleaning solution and a complex base coupled to the reservoir to insure a hermetically closed reservoir environment. The complex base is separated into at least a first and a second segment. A lens holder assembly holds the lenses within the solution and is coupled to the complex base in the first segment. A motor is located in the second segment of the complex base to selectively introduce a catalyst to the cleaning solution. The cleaning system has additional features that permit the system to allow for the storage of the contact lenses by converting a neutralized cleaning solution into a storage solution to prevent recontamination.

19 Claims, 11 Drawing Sheets

(56) References Cited

U.S. PATENT DOCUMENTS

| | | |
|---|---|---|
| 4,990,517 A | 2/1991 | Petersen et al. |
| 5,051,509 A | 9/1991 | Nagano et al. |
| 5,059,597 A | 10/1991 | Petersen et al. |
| 5,117,849 A | 6/1992 | Zimmerli |
| 5,395,944 A | 3/1995 | Petersen et al. |
| 5,416,096 A | 5/1995 | Petersen et al. |
| 6,183,705 B1 | 2/2001 | Chang |
| 2008/0276971 A1 | 11/2008 | Ifejika |
| 2010/0233023 A1 | 9/2010 | Kanner |

OTHER PUBLICATIONS

International Preliminary Report on Patentability issued by the IPEA/US in the corresponding PCT application PCT/US12/060119 dated Oct. 4, 2013.

* cited by examiner

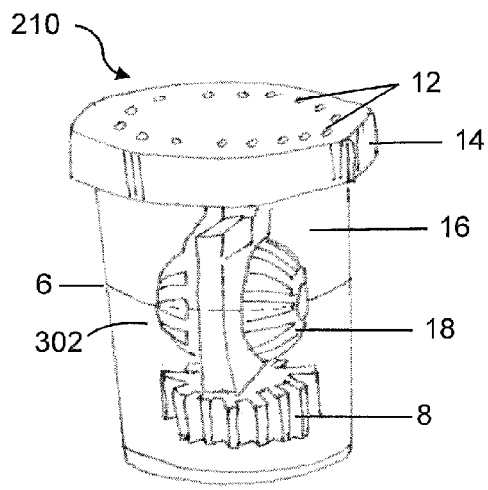
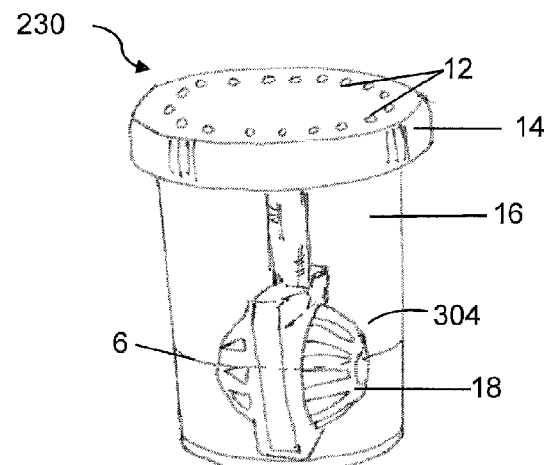
Figure 1A
(PRIOR ART)
Figure 1B
(PRIOR ART)
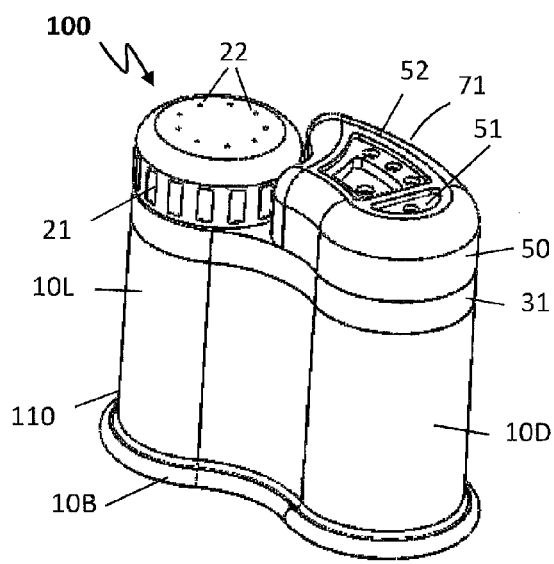
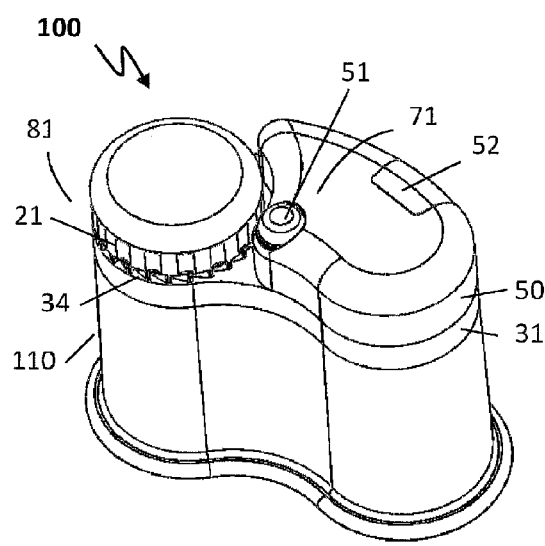
Figure 2A
Figure 2B

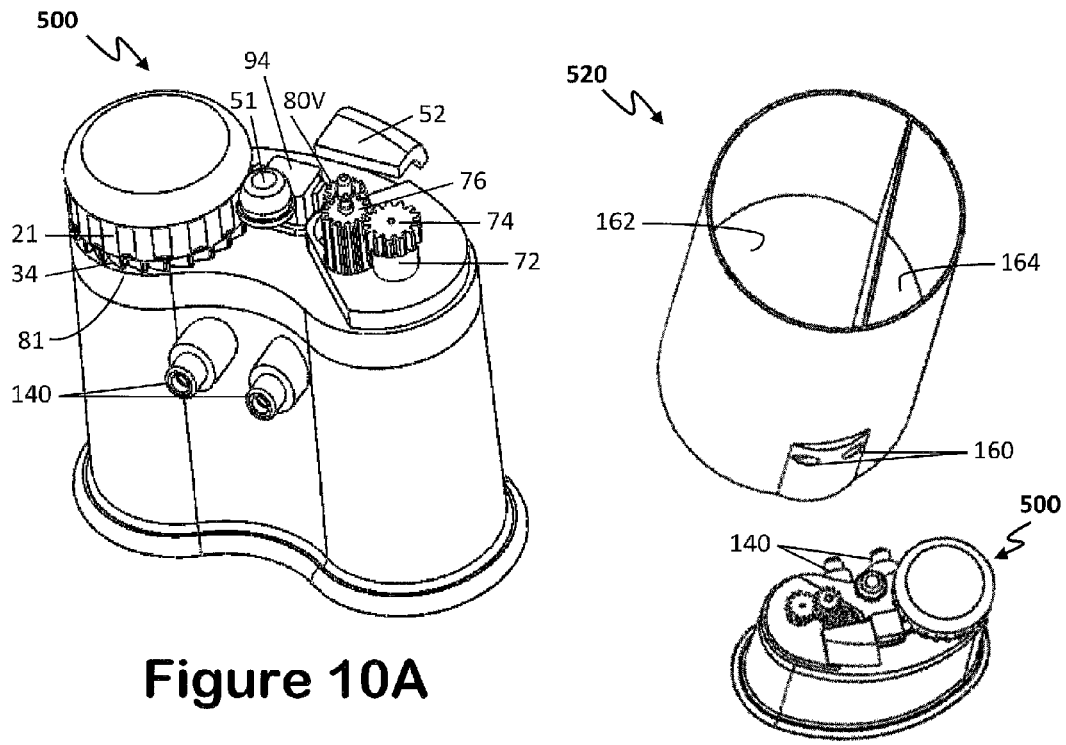
Figure 10A
Figure 10B
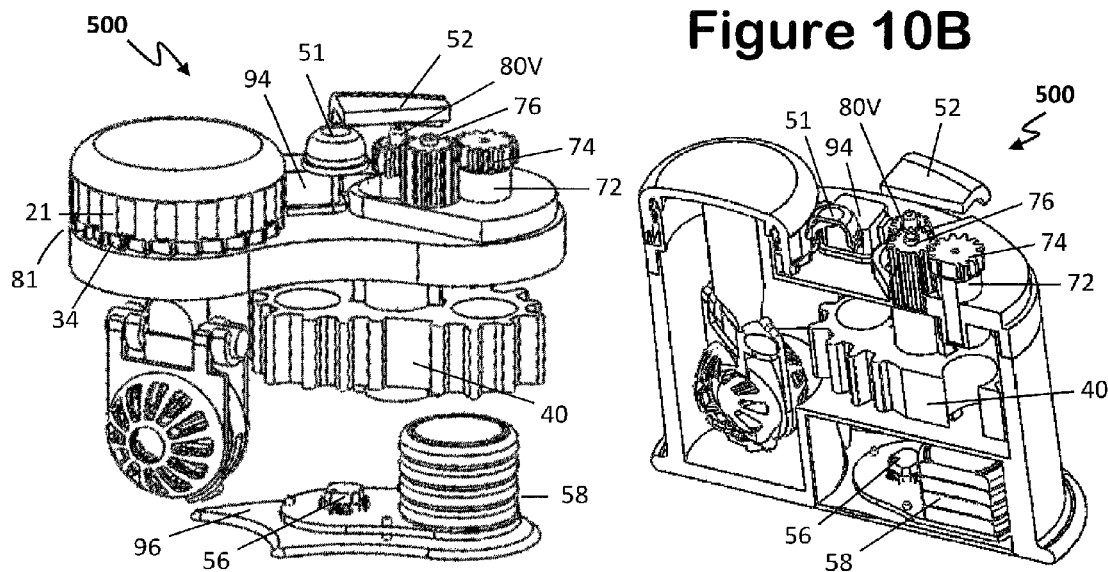
Figure 10C
Figure 10D

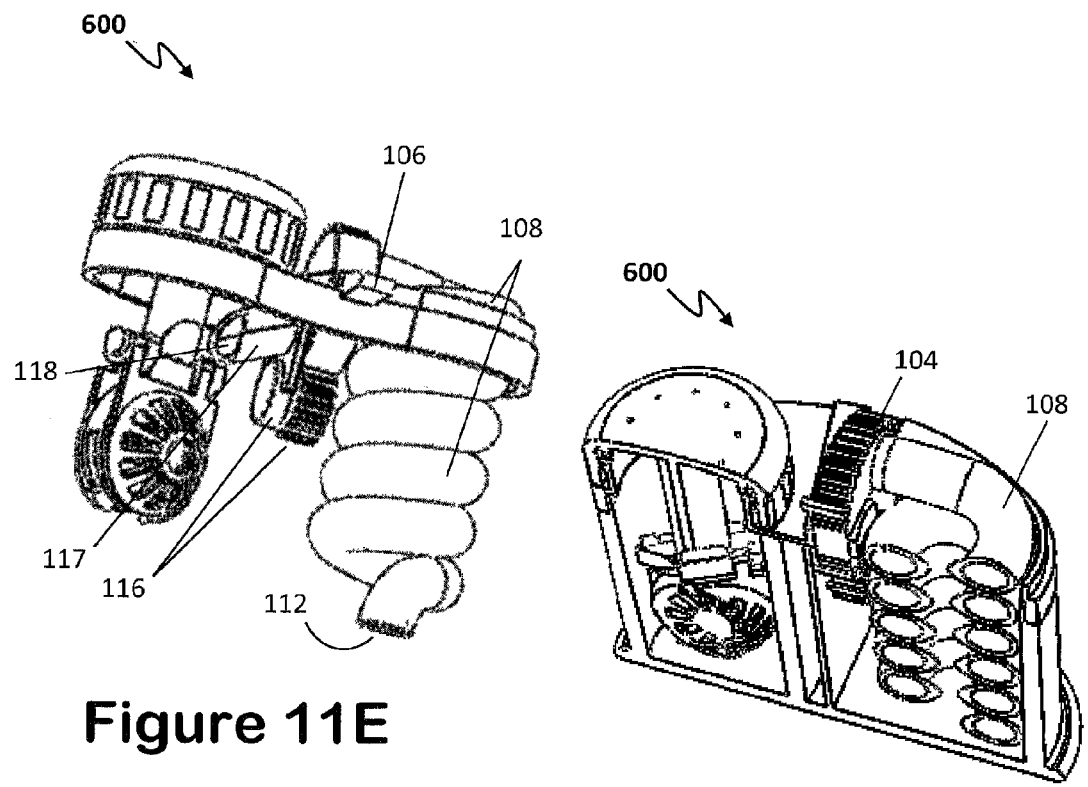
Figure 11E
Figure 11F
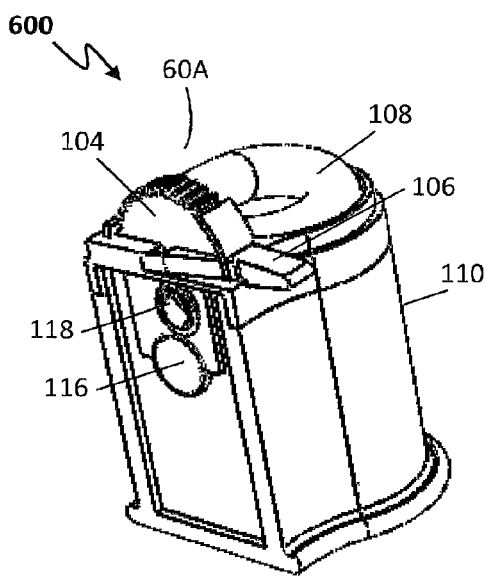
Figure 11G
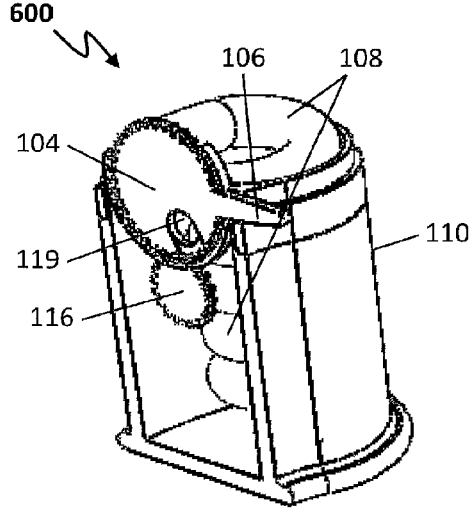
Figure 11H

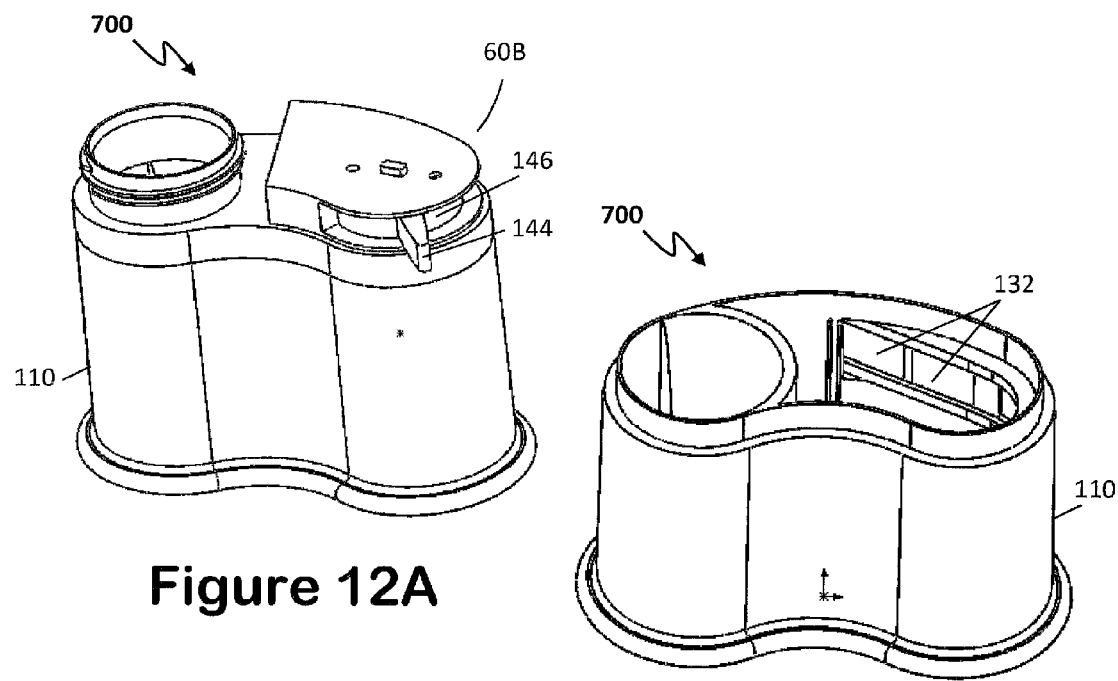
Figure 12A
Figure 12B
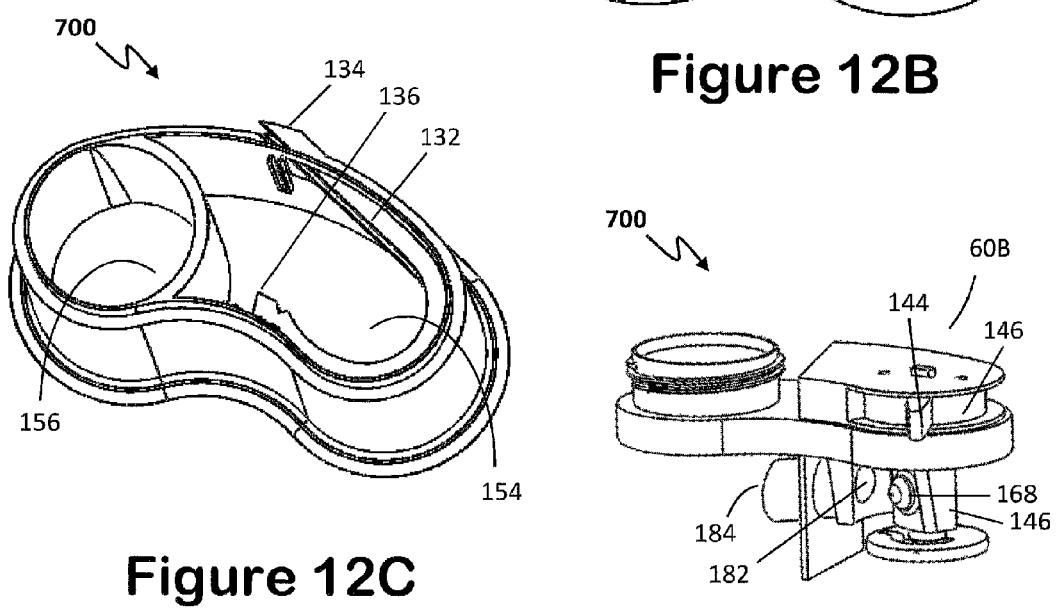
Figure 12C
Figure 12D

CONTACT LENS CLEANING SYSTEMS

CROSS-REFERENCE TO RELATED APPLICATION

This application claims the benefit of priority under 35 U.S.C. §119(e) to U.S. Provisional Application Ser. No. 61/546,284, titled "Container for Contact Lens Solutions" filed Oct. 12, 2011, which is hereby incorporated by reference in its entirety.

TECHNICAL FIELD

The present disclosure relates in general to the field of Ophthalmology and, more particularly, to contact lens cleaning systems.

BACKGROUND

Contact lenses need to be cleaned/disinfected in order to remove microbes, proteins, lipids and other debris from the surfaces of the lenses. Two classes of contact lens cleaning/disinfecting solutions are commonly available for use with soft contact lenses: the class of the multipurpose disinfecting solutions (MPDS) and the class of the hydrogen peroxide solutions.

Concerns over the use of hydrogen peroxide systems involve ocular toxicity and recontamination. Firstly, hydrogen peroxide is harmful for the eyes. Therefore, hydrogen peroxide systems need to neutralize the hydrogen peroxide solutions through a catalyst prior to lens wear. Premature removal of lenses from the solution prior to full neutralization may lead to ocular toxicity. Some systems that may adequately provide means for neutralizing the hydrogen peroxide fail with respect to the second concern. Secondly, hydrogen peroxide systems are not storage solutions. Following neutralization, hydrogen peroxide solution becomes water (and $O_2$ which leaves the cup through little holes in the cap). Water typically fails to provide contact lenses with adequate protection from contamination when stored for selected periods of time. Lenses should generally be removed from the neutralized solution and worn relatively soon thereafter. Long delays in removing the lenses from the cup, which now contains unprotected water, may cause re-contamination of the lenses with opportunistic microbes. In contrast, a MPDS solution can act as a good storage solution but typically has less disinfecting power against certain fungi and especially fungi cysts.

There are two commonly available $H_2O_2$ systems: the one-step $H_2O_2$ system and the two-step $H_2O_2$ system. In the one-step $H_2O_2$ system, the catalyst neutralizes the hydrogen peroxide solution from the start of the process, while in the two-step $H_2O_2$ system, the neutralizing catalyst is added at the end of the disinfection phase. While the two-step $H_2O_2$ systems were shown to be more effective disinfecting solutions than the MPDS and the one-step $H_2O_2$ systems, two-step systems tend to fall out of favor mainly due to the need for the extra step needed to neutralize the $H_2O_2$ solution. Furthermore, conventional two-step systems typically fail to provide a safe system to avoid ocular toxicity and recontamination. Although great strides have been made in contact lens cleaning systems, considerable shortcomings remain.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which:

FIG. 1A is a simplified schematic, tridimensional, general illustration showing a lens case commonly used in a one-step $H_2O_2$ system (Prior Art);

FIG. 1B is a simplified schematic, tridimensional, general illustration showing a lens case commonly used either in a one-step $H_2O_2$ system or in a two-step $H_2O_2$ system (Prior Art);

FIGS. 2A through 2D are simplified schematic, tridimensional illustrations showing some elements and possible example details and potential operation in accordance with one or more embodiments of the present disclosure;

FIGS. 10A through 10D are simplified schematic, tridimensional illustrations showing elements, specific parts and possible example details and potential operation in accordance with one or more embodiments of the present disclosure;

FIGS. 11A through 11H are simplified schematic, tridimensional illustrations showing elements, specific parts and possible example details and potential operation in accordance with one or more embodiments of the present disclosure; and FIGS. 12A through 12D are simplified schematic, tridimensional illustrations showing elements, specific parts and possible example details and potential operation in accordance with one or more embodiments of the present disclosure.

DETAILED DESCRIPTION OF EXAMPLE EMBODIMENTS

Overview

Figure 2C:
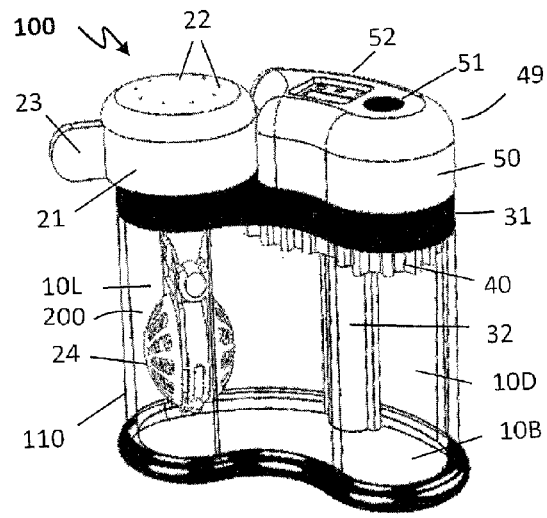

An apparatus for use with contact lenses is provided in one example and includes a contact lens cleaning system for cleaning and disinfecting contact lenses, wherein the contact lens cleaning system contains a reservoir, a lens holder assembly, and one or more mechanisms associated with the operation of the contact lens cleaning system. In more particular instances, the contact lens cleaning system can have a physical shape which is both secured and ergonomic.

In other implementation, the contact lens cleaning system can have a general kidney-like structure. In other examples, the contact lens cleaning system can have a general round or oval structure.

In more particular instances, the contact lens cleaning system can have elements associated with user's compliance. In other instances, the contact lens cleaning system can have elements associated with user's safety.

Additionally, the contact lens cleaning system can have a locking system configured to selectively prevent the lens holder assembly from being removed from the reservoir during an unsafe condition. The locking system is driven by a drive mechanism and may be either a mechanical type system or an electrical type system. In some instances, the locking system may be overridden by a user during the cleaning or storage process.

Furthermore, the drive system of the contact lens cleaning system controls the automated features of the cleaning system and storage systems, such as a user interface, a catalyst, and a concentrate dispensing system. The drive system selectively delivers and removes a catalyst from the cleaning solution. The user interface provides user feedback regarding the phases of operation of the cleaning system. In other instances, the drive system regulates a concentrate dispensing system to permit the safe storage of the contact lenses. The concentrate dispensing system may use an internal reservoir for holding concentrated storage solution or an external reservoir holding both cleaning solution and concentrate storage solution.

To use the cleaning system, contact lenses are inserted into a lens holder assembly which is then coupled to a complex base. The complex base surrounds and seals a reservoir to ensure a hermetically closed reservoir environment. The complex base has at least two segments. The lens holder is located within a first segment. The reservoir is filled and a catalyst is introduced into the cleaning solution. The catalyst enters the cleaning solution from a second segment of the complex base.

In some instances, the method may include locking the lens holder assembly to prevent removal of the contact lenses during an unsafe condition. The locking system may also be a mechanical type system or an electrical type system. In selected instances, the locking system may be overridden by a user.

Additionally, the method may include activating a drive mechanism to activate and selectively control the cleaning system. The drive mechanism may automatically fill the reservoir with cleaning solution and control the movement of the catalyst.

A user may receive user feedback regarding the phases of operation of the cleaning system and/or storage system through a user interface. The user interface may include digital displays and lighting representing selected information.

In other instances, the method can include injecting a concentrated storage solution into a neutralized cleaning solution to avoid recontamination of the lenses during storage. Doing so permits the lenses to be stored in a safe environment.

Furthermore, other instances of the method may include coating components of the cleaning system with antibacterial agents to prevent microbial growth on selected surfaces of the cleaning system.

Example Embodiments

Turning to FIG. 1A, FIG. 1A is a simplified, schematic tridimensional illustration of a common contact lens case 210 for cleaning contact lenses. Contact lens case 210 is representative of the one-step hydrogen peroxide systems where contact lens disinfection and hydrogen peroxide neutralization occur simultaneously. Contact lens case 210 includes a cup 16 and a lens holder assembly 302. Lens holder assembly 302 includes a cap 14, lens basket system 18, and a neutralizer—a platinum-coated disc 8—at its distal end. In operation, contact lenses are placed in lens basket system 18 and cup 16 is filled with 3% hydrogen peroxide solution up to line 6, which is marked on the cup wall. Lens holder assembly 302 is then immersed in the hydrogen peroxide solution within cup 16, and cap 14 is closed. Disinfection of contact lenses by the hydrogen peroxide solution then takes place simultaneously with the break-down (neutralization) of the same hydrogen peroxide solution, catalyzed by the platinum-coated disc 8, into water and oxygen; the later escapes the system through holes 12 on top of cap 14.

FIG. 1B is a simplified, schematic tridimensional illustration of another common contact lens case 230 for cleaning contact lenses. Contact lens case 230 includes a cup 16 and a lens holder assembly 304. Lens holder assembly 304 includes a cap 14 and a lens basket system 18. In operation, contact lenses are placed in lens basket system 18 and cup 16 is filled with 3% hydrogen peroxide solution up to line 6, which is marked on the cup wall. A tablet, containing the enzyme catalase, is then thrown into the hydrogen peroxide solution followed by immersing lens holder assembly 304 in the hydrogen peroxide solution within cup 16 and closing cap 14. Here, again, disinfection of contact lenses by the hydrogen peroxide solution occurs simultaneously with the break-down (neutralization) of the same hydrogen peroxide solution, catalyzed by the enzyme catalase, into water and oxygen; the later escapes the system through holes 12 on top of cap 14.

Common contact lens case 230 can, however, be part of a two-step hydrogen peroxide system simply by delaying the introduction of the tablet containing catalase after contact lens disinfection is complete. The two-step system thus described allows for a full disinfection phase to take place following with a separate neutralization phase, where hydrogen peroxide is broken down into water and oxygen.

Consequently, the two-step hydrogen peroxide systems are shown to be very efficient disinfecting solutions; for example, by killing large inocula of *Acanthamoeba* cysts—the resistant form of this amoeba. The one-step hydrogen peroxide systems, on the other hand, are less effective than the two-step hydrogen peroxide systems and their disinfecting action was compared to that of the common multi-purpose disinfecting solution.

From the data available and from an antimicrobial disinfection perspective, it is concluded that use of two-step $H_2O_2$ solutions should be the solution of choice.

Disadvantages of use of the two-step hydrogen peroxide system may include (a) wearer's either inadvertent failure to neutralize the hydrogen peroxide solution or premature removal of lenses from the system, thus suffering pain and trauma associated with putting hydrogen peroxide into the eyes, (b) wearer's use of hydrogen peroxide solution as it were multi-purpose solution for cleaning and rinsing of contact lenses, and (c) the extra procedure needed to be performed by the wearer when using the two-step hydrogen peroxide, which probably make these solutions fall out of favor.

Given the above, there is a need for a system that encourages contact lens wearers to use the effective two-step hydrogen peroxide system while addressing its disadvantages. Hence, the objective of this disclosure is to provide such a solution by presenting a contact lens cleaning system, which functions as a two-step hydrogen peroxide system while, for the user, it functions as a one-step system.

In general, embodiments of the present disclosure present a system for the disinfection and/or cleaning of contact lenses. The contact lens cleaning system can comprise a reservoir, a complex base, moving components, one or more mechanical or electro-mechanical mechanisms, a cap and a lens holder assembly.

Turning to FIGS. 2A through 2D, FIGS. 2A-2D are simplified schematic, tridimensional illustrations showing one embodiment of cleaning system 100. Cleaning system 100 includes at least: a reservoir 110, a lens holder assembly 200, a controller/timer trigger motor 60, and a user interface 71. The following figures disclose a plurality of embodiments and features associated with various cleaning systems of the present application. It is understood that any of the features disclosed in the present application may be utilized and incorporated into any cleaning system embodiment disclosed herein.

Figure 2D:
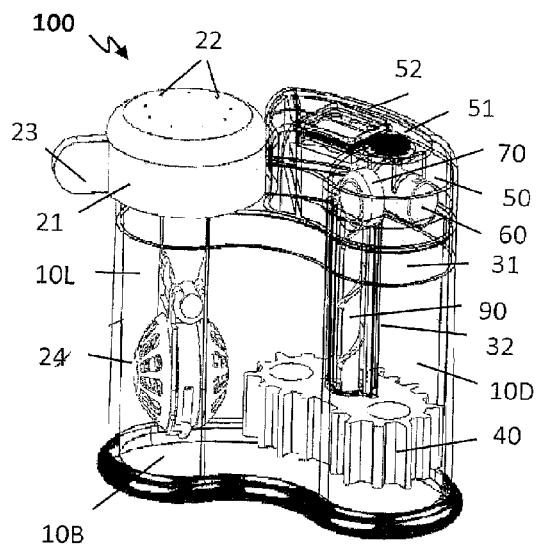
Figure 3A:
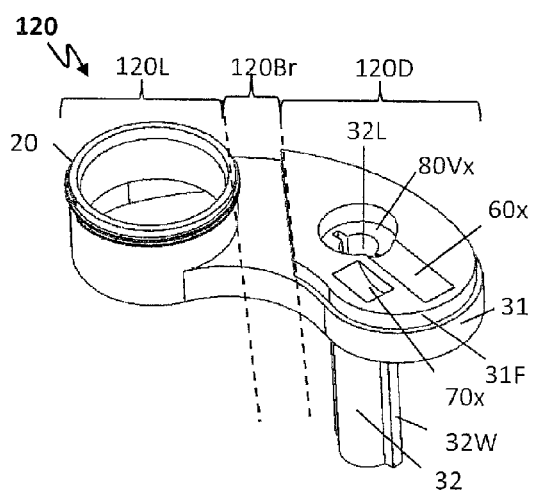
FIGS. 3A and 3B are simplified schematic, tridimensional illustrations showing specific parts, elements and possible example details and potential operation in accordance with one or more embodiments of the present disclosure.
Figure 3B:
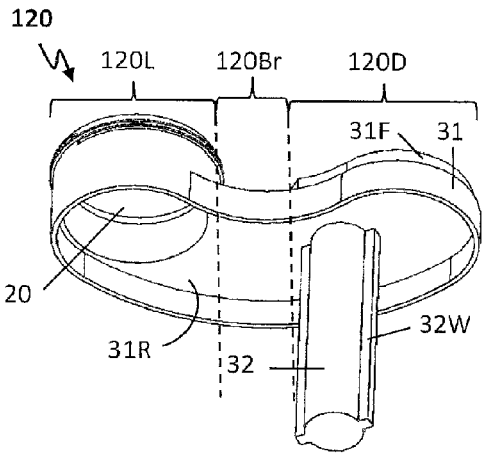

Contact lens cleaning system 100 may be made from compatible plastic materials, generally kidney shaped or oval shaped apparatus designed to be ergonomic and have good physical stability. Contact lens cleaning system 100 has a reservoir 110 (FIGS. 2A and 2B) having substantially a shape suitable for containing the disinfecting solution, part of the moving components, and the lens holder assembly 200 (FIGS. 2C and 2D). Reservoir 110 substantially has a base 10B, at its bottom, and a top circumferential strip area, which fits encircling wall 31 of complex base 120 (FIGS. 3A and 3B). While a one entity, reservoir 110 is generally divided into a lens side 10L, to accommodate the lens holder assembly 200 (FIG. 6), and a disc side 10D, to accommodate drive means 48 the vertical shaft 32 (FIG. 3C) and the moving platinum-coated disc 40 (FIGS. 2C and 2D). Reservoir 110 may be opaque or transparent and may be constructed from a material which is substantially compatible with the disinfecting solution and contact lens materials.

Complex base 120 (FIGS. 3A and 3B) has substantially an encircling wall 31, a cylindrical opening 20, and a raised area 31F. Encircling wall 31, having identical circumferential shape to that of reservoir 110, matches and is attached to the top circumferential strip area of reservoir 110 by means of, including but not limited to, glue, heat or a combination thereof, to insure a hermetically closed reservoir environment. Complex base 120 (FIG. 3A) may be generally divided into 3 segments: lens segment 120L, which is vertically aligned with the lens side 10L of reservoir 110 (FIG. 2A); disc segment 120D, which is vertically aligned with disc side 10D of the reservoir 110 (FIG. 2A); and bridge segment 120Br, which connects lens segment 120L with disc segment 120D. Lens segment 120L is substantially made of a short, vertical, open cylinder 20 (FIGS. 3A and 3B) having top and bottom ends. While the bottom end opens into the bottom surface of complex base 120 (31R, FIG. 3B), the top end is equipped with a fitting means, including but not limited to, a thread designed to fit and quickly (turning the cap only a quarter circle) lock cap 21 of lens holder assembly 200 (FIGS. 2A-2D, 4B, 6, 7A-7C, 9A-9B, 10A-10D, and 11A-11F) in place. The top part of disc segment 120D of complex base 120 (FIG. 3A) is substantially composed of a raised surface 31F, serving as the floor of a mechanism chamber 49, which is designed to precisely mate the encircling wall of cover 50 of the mechanism chamber 49 (FIG. 2A-2D). Encircling wall of cover 50 and the side area of floor 31F (FIGS. 3A and 3B) of the mechanism chamber 49 are attached by means of, including but not limited to, glue, heat, or a combination thereof to insure a hermetically closed mechanism chamber.

Figure 8A:
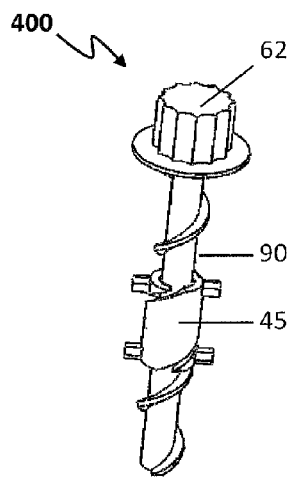
FIGS. 8A and 8B are simplified schematic, tridimensional illustrations showing specific parts, elements and possible example details and potential operation in accordance with one or more embodiments of the present disclosure.

Floor 31F of the mechanism chamber 49 (FIG. 3A) has a few depressions and holes to allow for the housing and operation various components. A drive mechanism 67 is configured to control the cleaning process and storage process of the cleaning systems of the present application. In doing so, drive mechanism 67 controls the automated activities within the cleaning and storage systems. Motor 60, as well as systems 60A and 60B described later, are types of drive mechanisms 67. Floor 31F has substantially a motor depression 60x to accommodate motor 60 and motor gear 80H (FIGS. 2D and 4B), a battery depression 70x to accommodate battery 70 (FIGS. 2D and 4B), a vertical gear depression 80Vx to accommodate vertical gear 80V (FIGS. 4A and 4B), and a uni- or bi-winged hole 32L leading downward into a lumen within vertical shaft 32 to accommodate vertical spiral shaft drive 90 and accompanying magnet body 45 (FIG. 8A). The bottom part of disc segment 120D of complex base 120 (FIG. 3B) exhibits the encircling wall 31, the base recess area 31R, and the exterior of the hollow vertical shaft 32 with its lateral wings 32W.

Figure 4A:
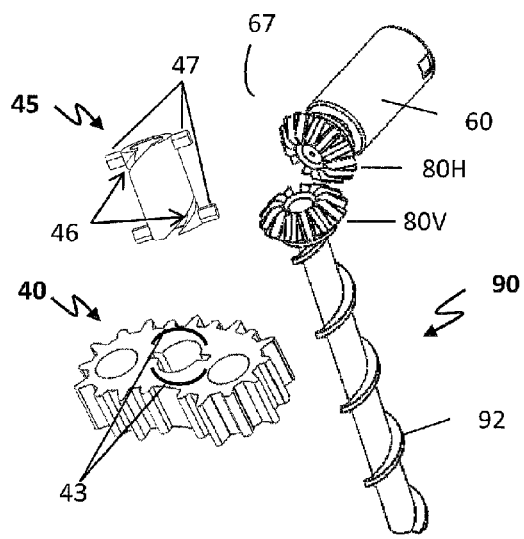
FIGS. 4A and 4B are simplified schematic, tridimensional illustrations showing other specific parts, elements and possible example details and potential operation in accordance with one or more embodiments of the present disclosure.

As shown in FIGS. 4A and 8A, in one or more embodiments of the present disclosure, magnet body 45 substantially has a cylindrical shape, inner spiral threads 46, which fit external spiral threads 92 of spiral shaft drive 90 (FIG. 4A), and lateral projections 47, which are designed to fit and run along the lumen of wings 32W of vertical shaft 32 (FIGS. 3A and 3B). Iron-embedded, platinum-coated disc 40 (FIGS. 4A and 4B) is designed to travel along external surface of vertical shaft 32 by being magnetically attracted, through the wall of vertical shaft 32, to magnet body 45, which travels inside the lumen of vertical shaft 32 along spiral shaft drive 90 rotation of which driven by motor 60.

Figure 4B:
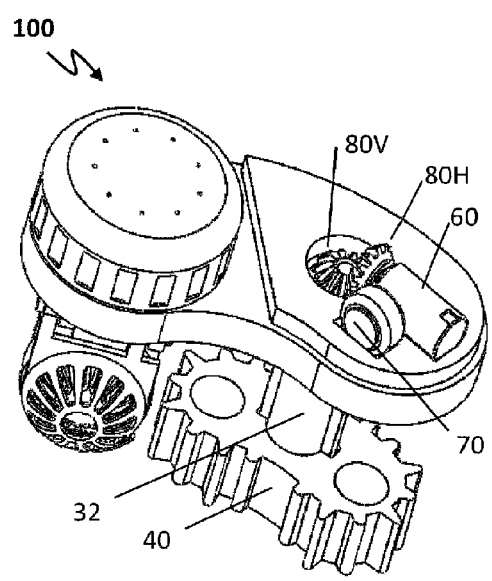

Iron-embedded, platinum-coated disc 40 (FIGS. 4A and 4B) is substantially made of compatible materials, including but not limited to, plastic, in any tridimensional shape and form, which would increase its surface area. Disc 40 substantially has a central uni- or bi-winged throughout hole designed to accommodate and slide on a uni- or bi-winged external surface of vertical shaft 32 (FIG. 4B). Also, disc 40 may have one or more additional holes designed to adjust the disc weight for proper movement along the exterior surface of vertical shaft 32 and increase surface area. Circular or semicircular metal sheets 43 made of, including but not limited to iron, are embedded in the plastic of disc 40 in proximity of the central uni- or bi-winged hole such that they can be magnetically attracted by the moving magnet body 45 along vertical spiral shaft drive 90 (FIG. 8A) and move disc 40 down (FIG. 2D) and up (FIG. 2C) the external surface of vertical shaft 32 at start and end of neutralization phase, respectively. For clarification: the terms 'iron-embedded' and 'platinum-coated' are used here and throughout this document only for convenience and do not imply any restriction to the sole use of these materials. Any magnetically attractable material may replace iron and any transition metal or any other agent, capable of catalyzing the neutralization of hydrogen peroxide, may replace platinum. Also, while throughout this disclosure the magnet entity is described as a cylindrical body traveling inside the lumen of vertical shaft 32 and metal sheets are embedded within the plastic disc, this is not to limit the vice versa situation, where magnet sheets are embedded within the plastic disc and the cylindrical body traveling along the lumen of vertical shaft 32 is made of one or more magnetically attractable metals or other materials.

FIGS. 2A, 2B, 5A, 5B, and 11A show some potential details of mechanism cover 50 of contact lens cleaning system 100 of one or more embodiments of the present disclosure. Cover 50 may be either transparent or opaque and may have substantially any desired shape. In general, cover 50 is equipped with a user interface 71 with depressions, excavations and holes to accommodate components of the mechanism, display, and control. User interface is configured to provide user feedback regarding the phases of operation of the contact lens cleaning system, as well as activate the cleaning system as described in any of the embodiments of the present application. Top area 50T of cover 50 (FIG. 5A), for instance, may substantially have excavation 51x for the ON/OFF rubber button 51 (FIG. 2C), an excavation 52x for LCD display 52 (FIG. 2C), an excavation 53x for LCD screen 53 (FIG. 2C), and holes in these excavations. Holes (FIGS. 5A and 5B) may include a rubber button hole, within excavation 51x, to accommodate the lower projection of rubber button 51 and wiring thereof; one or more connector holes, within excavation 52x, to connect LCD display 52 with an underlined circuit board (not shown); and holes within excavation 53x, for one or more LED indicators, to accommodate the LEDs themselves and their wiring connections with an underling circuit board. Cavity 50C, delineated by wall 54, of cover 50 (FIG. 5B) may substantially be provided with elements that support and/or fix in place components of the mechanism chamber. One such element is the motor support projection pair 60S (FIG. 5B) that substantially hold the body of motor 60 (FIG. 4B) in place. Also, accommodated within cavity 50C, and may substantially be attached to the inner top surface of cover 50, is the mechanism's circuit board and wiring thereof (not shown), designed to control the overall automated operation of the contact lens container. For clarification, location of elements which may control one or more functions of the contact lens cleaning system of the present disclosure is not limited to the mechanism chamber. They me be found, in one or more embodiments of the present disclosure, anywhere in the contact lens cleaning system. For instance, in a special recess or cavity at the bottom of the contact lens cleaning system as depicted in FIGS. 10C and 10D, where printed circuit board 96 and controller 56 are located in an inclusion on the bottom of reservoir 110 along with batteries 58.

Figure 5A:
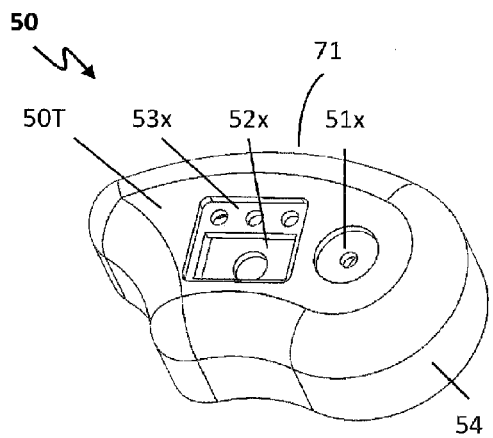
FIGS. 5A and 5B are simplified schematic, tridimensional illustrations showing other specific parts, elements and possible example details and potential operation in accordance with one or more embodiments of the present disclosure.
Figure 5B:
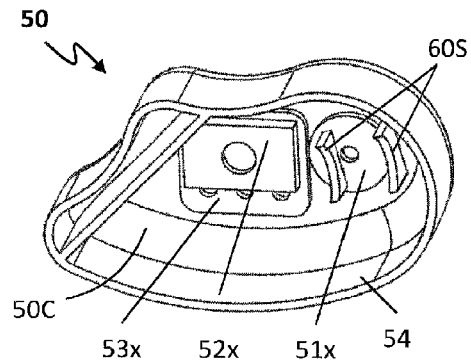

In one or more embodiments of the present disclosure, the contact lens cleaning system may include different shapes of LCD 52 (FIGS. 2A and 2B) and one or more LED lights (FIGS. 2C and 5A). These LCDs and LEDs may provide information about time, status of the various phases of operation of the contact lens cleaning system (e.g., disinfection, neutralization, completion, and storage status) and information, which may be related to user's safety or function of the contact lens cleaning system.

Many designs of lens holder assembly 200 and cap 21 (FIG. 6) may be incorporated in one or more embodiments of the present disclosure. Contact lens cleaning system 100 (FIG. 2A) for instance, presents cap 21 as having a rough circumferential surface to hold on while closing or opening the cap. This cap may have one or more simple or tortuous holes 22 for the escape of oxygen produced during neutralization of hydrogen peroxide solution. Also, cap 21 may have one or more locking or latching systems 81, including but not limited to, mechanical types such as a serrated circumferential area 34 (FIGS. 2B, 7A-7E, 9A, 9B, and 10A-10D) and electrical types such as the cap electric latch 94 depicted in FIGS. 10A-10D for one embodiment 500 of the present disclosure. Locking systems 81 are configured to selectively prevent removal of lens holder assembly 200 from reservoir during any unsafe condition. An unsafe condition refers to periods of time where either the lenses are contaminated or potentially contaminated (after neutralization as a result of storage) or the cleaning solution has not been sufficiently neutralized, thereby preventing a user from inserting hydrogen peroxide solution into the eye. In another embodiment with cap 21, cap 21 may present a thumb tab 23 (FIGS. 2C, 2D, and 6) for an easier cap operation. Inner threads of cap 21 and outer threads of cylinder 20 (FIG. 3A) along with cap locking systems 81 including, but not limited to, cap locking mechanisms 34 (FIGS. 9A and 9B) and 94 (FIGS. 10A and 10B) and other mechanical or electrical features are designed to provide a quick, quarter circle cap locking/unlocking operation.

Figure 6:
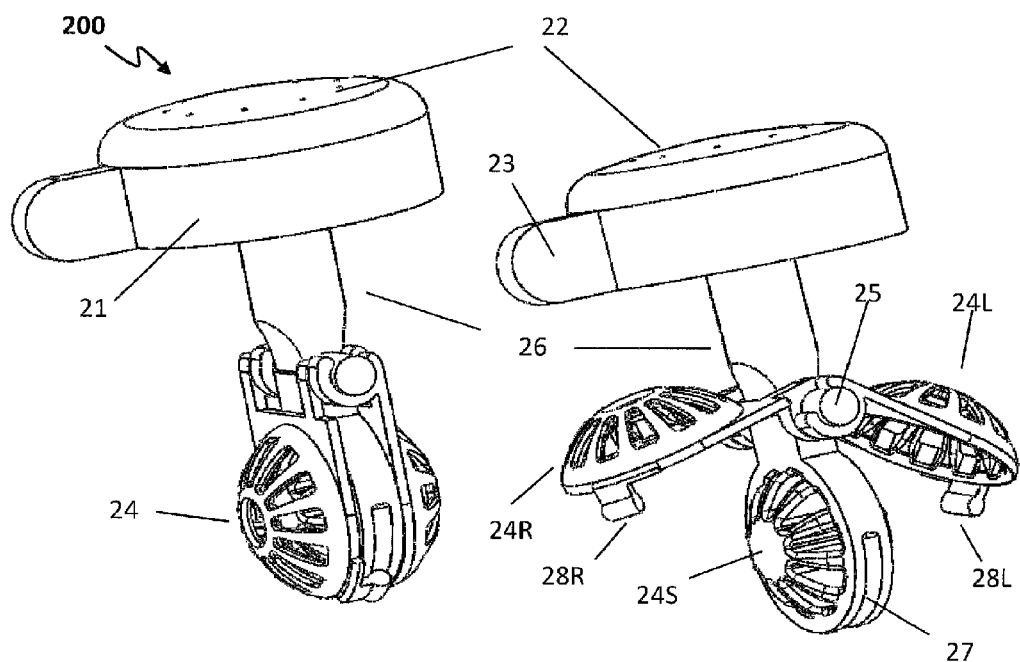
FIG. 6 is a simplified schematic, tridimensional illustration further showing specific parts, some elements and possible example details and potential operation in accordance with one or more embodiments of the present disclosure.

FIG. 6 is a simplified schematic, tridimensional illustration showing specific parts, some elements and possible example details and potential operation of lens holder assembly 200 in accordance with one or more embodiments of the present disclosure. Lens holder assembly 200 is configured to locate and releasably secure lenses within reservoir 110. Lens holder assembly 200 is composed of cap 21 with holes 22, for the release of oxygen gas generated during the neutralization of hydrogen peroxide, on its top area; and thumb tab 23 to open and close the cap onto opening 20 of lens segment 120L of complex base 120 (FIG. 3A). Central shaft 26, originating from or attached to the inner surface of cap 21 (FIG. 6) ends distally with a fenestrated, bi-convex lens support body 24S having groove 27, which is adapted to lock in the right 24R and left 24L lens baskets 24 via their respective, 28R and 28L, locking elements. Shaft 26 is equipped with a transverse rod 25, which serves as a hinge for lens baskets 24R and 24L.

Below is a description of a potential operation of the contact lens cleaning system. It is provided here for illustration purposes only and, in no way, limits any of the scopes of operation of any of the embodiments of the present disclosure.

Pre-operation, right and left contact lenses are placed on lens support body 24S (FIG. 6) under baskets 24R and 24L, respectively, which are then closed and locked on locking groove 27. Reservoir 110 (FIG. 2C) is then filled with hydrogen peroxide solution up to a marked line, which is way below the bottom surface of the iron-embedded, platinum disc 40, which is in the up position, within base recess 31R (FIG. 3B). The lens-containing lens holder assembly 200 is then entered, through opening 20 of the complex base 120 (FIG. 3A), and immersed in the hydrogen peroxide solution at the lens side 10L of reservoir 110. Thumb tab 23 is then turned 90 degrees laterally—from the front, unlocked position—to lock cap 21. This contact lens cleaning system status is depicted in FIG. 2C.

Then a user activates motor 60 through user interface 71 to activate the contact lens cleaning system, including but not limited to, activating a controller, timer and LCD display, and turn on disinfection LED light 52. After a predetermined disinfection time [end of disinfection phase], the controller/timer trigger motor 60 to rotate its motor bevel gear 80H, which in turn engages and rotates vertical bevel gear 80V (FIG. 4B) and spiral shaft drive 90 (FIG. 4A). Male spiral threads 92 on spiral shaft drive 90 and female spiral threads 46 on the inner surface magnet body 45 (FIGS. 8A and 2D), along with magnet body lateral projections 47, move magnet body 45 and the magnetically attracted iron-embedded, platinum-coated disc 40 downward into the hydrogen peroxide solution [beginning of neutralization phase] (FIG. 2D). LED light indicating neutralization 52 is turned on. After a predetermined neutralization time [end of neutralization phase], the controller/timer trigger motor 60 to counter-rotate and pull disc 40 out of the neutralized solution, which is now substantially composed of water. At this point, the user may turn the thumb tab 90 degrees medially to the front side, to unlock cap 21, and open the basket cage to remove the clean contact lenses. If not removed within a predetermined time, the dedicated LED light will flash to alert the user to remove the lenses and either wear them or store them in a storage solution.

Figure 9A:
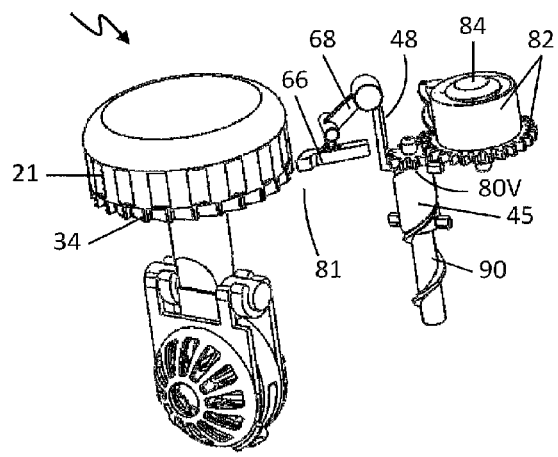
FIGS. 9A and 9B are simplified schematic, tridimensional illustrations showing other specific parts, elements and possible example details and potential operation in accordance with one or more embodiments of the present disclosure.
Figure 9B:
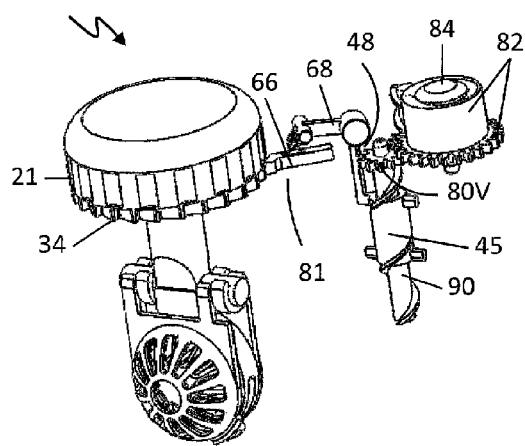

FIGS. 9A and 9B are simplified schematic, tridimensional illustrations showing another possible set of details and potential operation associated with locking and unlocking or cap 21 in one or more embodiments of the present disclosure. FIG. 9A shows contact lens assembly 200 with cap 21 and its serrated area 34. Upon 90 degree closure of cap 21, the cap 21 engages a locking system 81 composed of cap lock pivot arm 68 and cap lock slide 66 to prevent the user from inadvertent opening cap 21 prior to full neutralization (locked, FIG. 9B). In this embodiment, magnet body 45 possesses a vertical projection 48, which is an extension of one of its lateral projections. Post neutralization, iron-embedded, platinum-coated disc 40 raises to its up position in base recess 31R along with magnet body 45. At this point, magnet vertical projection 48 pushes cap lock pivot arm 68 upward to disengage cap lock slide 66 from the cap serrated area 34, thus unlocking cap 21 for the user to remove the contact lenses from the neutralized solution (unlocked, FIG. 9A).

Figure 7A:
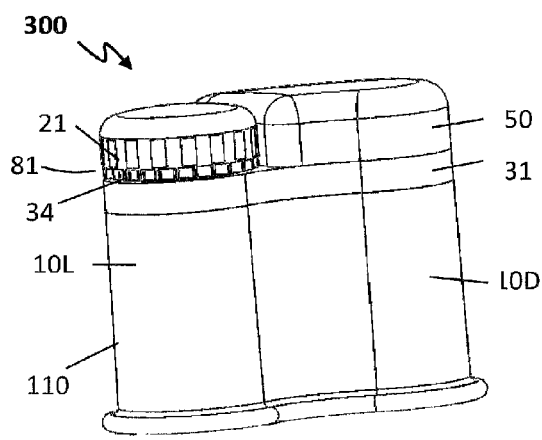
FIGS. 7A through 7J are simplified schematic, tridimensional illustrations showing elements, specific parts and possible example details and potential operation in accordance with one or more embodiments of the present disclosure.
Figure 7B:
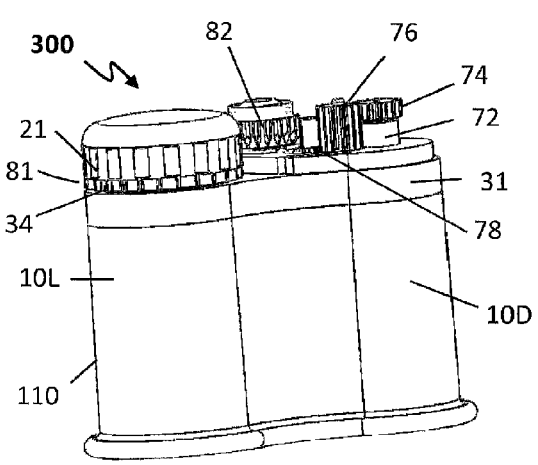
Figure 7C:
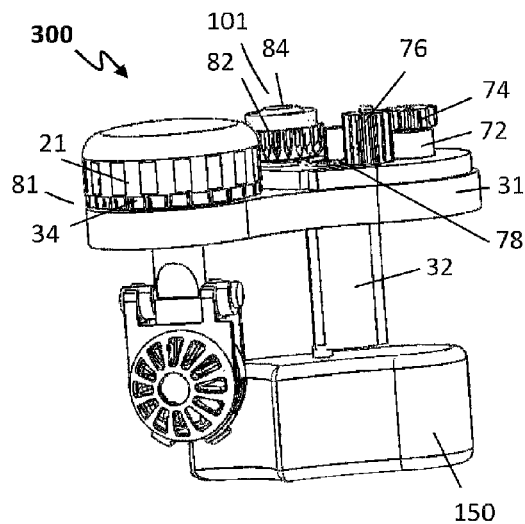
Figure 7D:
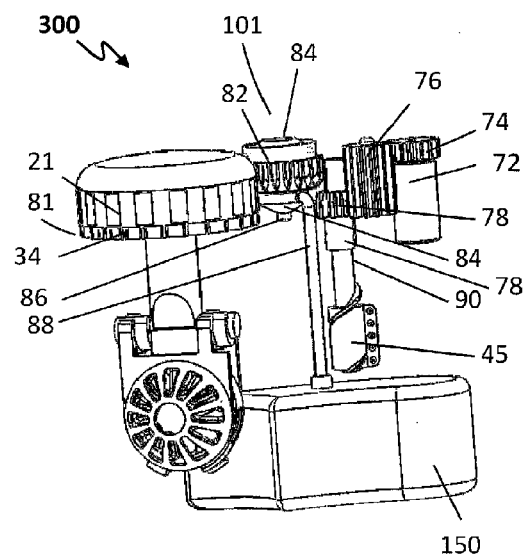
Figure 7E:
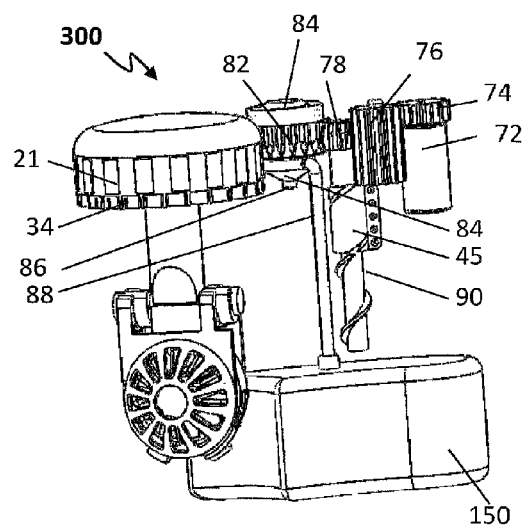
Figure 7F:
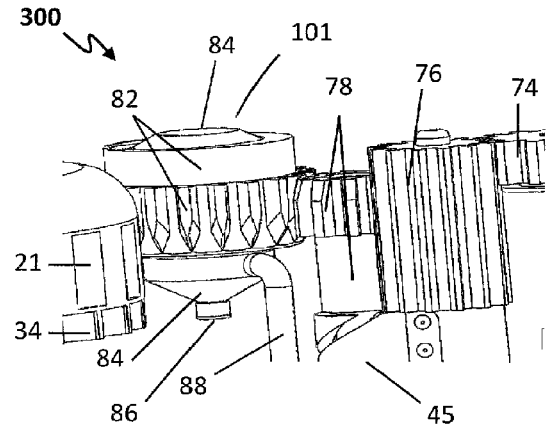
Figure 7G:
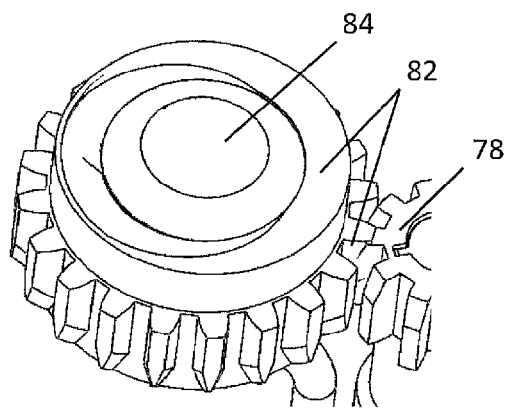
Figure 7H:
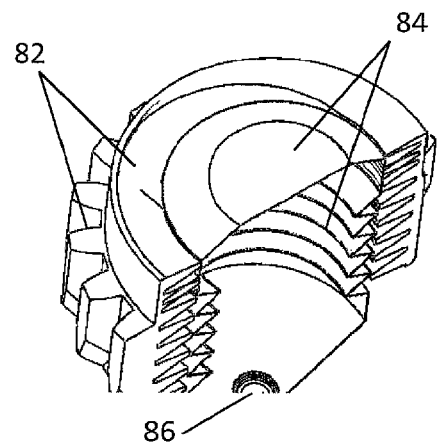
Figure 7:
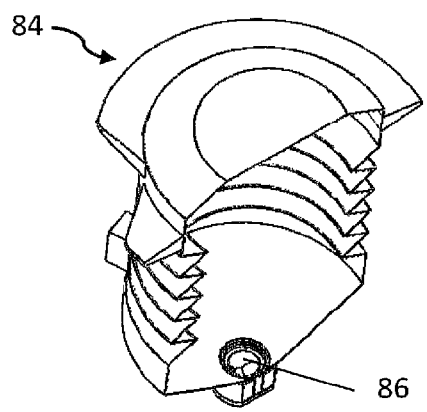
Figure 7J:
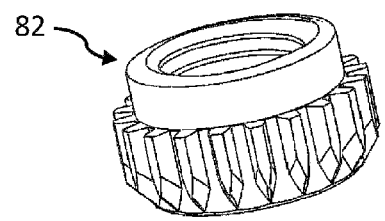
Figure 7J:
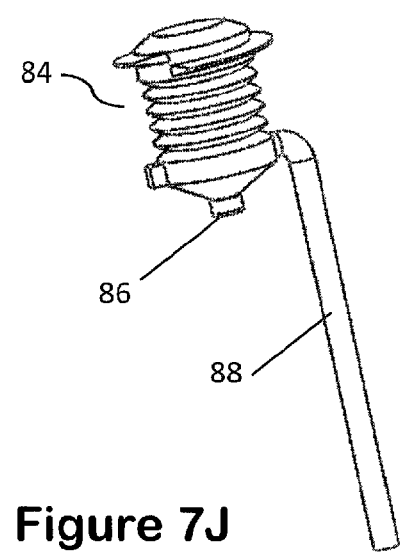

FIGS. 7A-7J are simplified schematic, tridimensional illustrations showing yet another possible set of details and potential operation associated with one or more embodiments of the present disclosure. FIGS. 7A-7J include contact lens cleaning system 300. Contact lens cleaning system 300 has many of the features of contact lens cleaning system 100. In addition, contact lens cleaning system 300 is equipped with one or more mechanisms designed to convert the neutralized hydrogen peroxide solution (basically, water) into a storage solution. The features specific for conversion of the resultant water into an effective storage solution are easily seen in FIGS. 7D-7F. FIG. 7D shows contact lens cleaning system 300 after removing reservoir 110, cover 50, and complex base 120 to expose details specific to this embodiment. Recalling, at the end of neutralization, the user needs to remove the lenses from neutralized solution (water) and wear or store them in a storage solution. In practice, if the user does not wear his/her contact lenses after they have been cleaned with a hydrogen peroxide solution, he/she is likely to leave them in the water. The unprotected water has been shown to contaminate with time, thus endangering the eyes of the unsuspecting lens wearer.

FIGS. 7A-7J show a possible set of details and potential operation, which is aimed at preventing such ocular complication. Turning to FIG. 7D, FIG. 7D shows a internal reservoir 150 containing concentrated multi-purpose disinfecting solution and a concentrate dispensing system 101 composed of a bellows 84, a connecting, long pipe 88, and a concentrate dispense bellows cylinder gear 82. Concentrate dispensing system is configured to create a suitable storage environment for the lenses following neutralization of the cleaning solution. In operation, motor 72 drives motor gear 74 to turn elongated intermediate gear 76 which, in turn, rotates a bellows lifting drive gear 78 to initially lower and raise the iron-embedded, platinum-coated disc 40 according to previously described magnetic operation. At the end of neutralization, when disc 40 is in the up position in base recess 31R, bellows lifting drive gear 78 (FIG. 7E) is pushed up to engage concentrate dispense bellows cylinder gear 82, and cap 21 is unlocked. A mechanism dedicated to detecting the vertical position of the cap, mediated by, but not limited to, LED beam informs the contact lens cleaning system controller about the status of cap 21. If cap is not lifted after a certain predetermined time, motor 72 actuates the gear chain system (FIG. 7E) to rotate bellows gear 82 to squeeze bellows 84, suck a small volume of concentrated multi-purpose solution from internal reservoir 150 through pipe 88, and squirt it through is check valve dispense outlet 86 into the resultant water, thus converting it to an acceptable, protecting, multi-purpose disinfecting solution, suitable of long term storage of contact lenses.

Figure 8B:
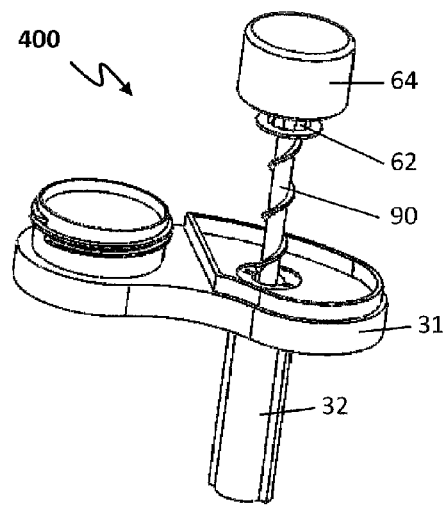

FIGS. 8A and 8B are simplified schematic, tridimensional illustrations showing yet another possible set of details and potential operation associated with one or more embodiments of the present disclosure. FIGS. 8A and 8B include elements specific for contact lens cleaning system 400. These elements comprise a vertical shaft gear 62 and a coupling gear and motor system 64 aimed at rotating vertical spiral shaft 90 and driving magnet body 45 and it accompanying disc 40 down or up.

FIGS. 10A through 10D are simplified schematic, tridimensional illustrations showing elements, specific parts and possible example details and potential operation in accordance with one or more embodiments of the present disclosure. FIGS. 10A through 10D demonstrate the potential use of external source of concentrated multi-purpose solution to convert the post-neutralization resultant water into an acceptable, protecting, storage solution. Also, one or more embodiment of the present disclosure provides a contact lens cleaning solution, which has the potential to avoid, or at least, reduce the inadvertent use of hydrogen peroxide solutions for rinsing contact lenses and injuring one's eyes. Turning to FIGS. 10A and 10B, FIG. 10A shows contact lens cleaning system 500 similar in shape and function to previously described systems in this document and a sealed, bi-compartmental bottle/canister 520 containing hydrogen peroxide in one compartment 162 and concentrated multi-purpose disinfecting solution in another compartment 164. Contact lens cleaning system 500 comprises a motor 72 and a set of gears similar to another embodiment of the present disclosure, which are aimed to lower and raise iron-embedded, platinum-coated disc 40. In Also, contact lens cleaning system 500 possesses a pair of electrical shuttered nozzles 140, designed to couple with the bottle's pair of one-way valves 160. In operation, lenses are placed in lens holder assembly, and cap 21 is closed/locked in place. Contact lens cleaning system 500 is then connected to sealed bottle 520 via nozzles 140 and valves 160. Once the ON button 51 is pressed, a precise volume of hydrogen peroxide solution moves from compartment 162 to contact lens cleaning system 500, through the respective nozzle and valve. After a predetermined time following neutralization, if cap 21 has not been lifted, the other shutter 160 of bottle 520 is open to deliver a predetermined small volume of concentrated multi-purpose solution to convert the resultant water into a protective storage solution.

Figure 11A:
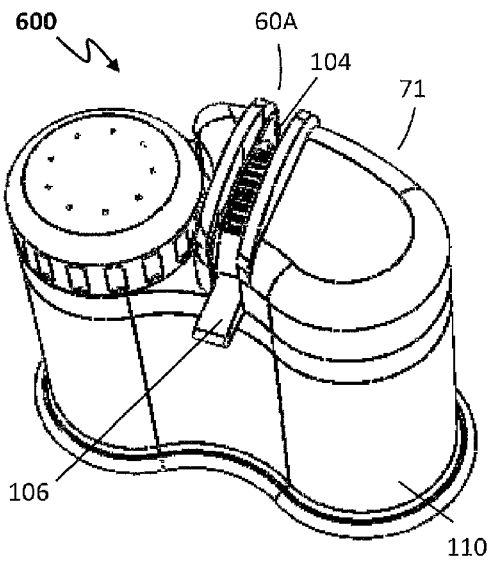
Figure 11B:
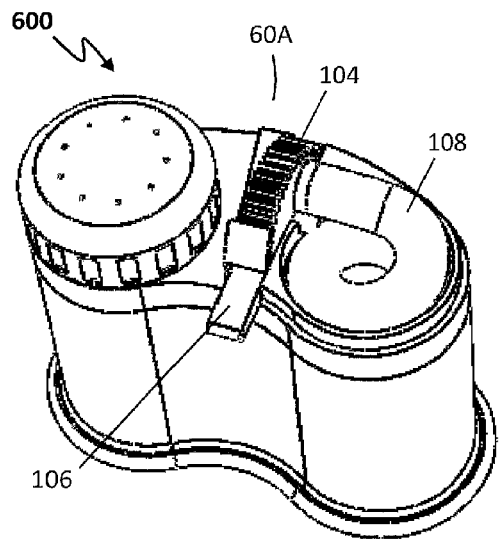
Figure 11C:
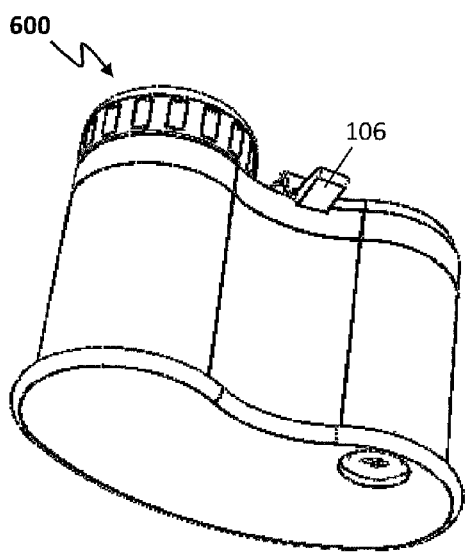
Figure 11D:
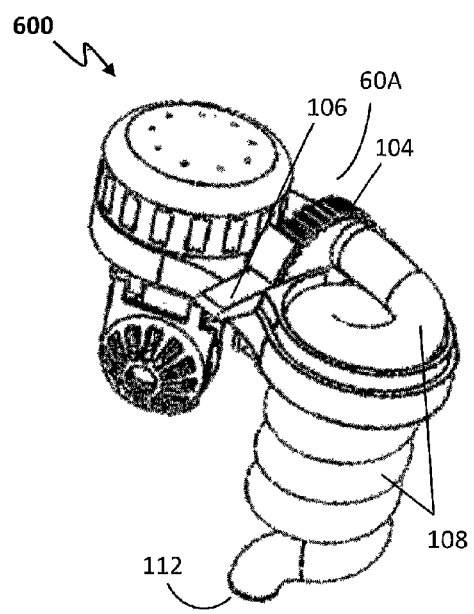

FIGS. 11A through 11H are simplified schematic, tridimensional illustrations showing elements, specific parts and possible example details and potential operation in accordance with one or more embodiments of the present disclosure. FIGS. 11A through 11H show contact lens cleaning system 600. Contact lens cleaning system 600 is mechanically operated and uses catalase tablets as neutralizing agents. FIGS. 11A through 11H illustrate motor 60A, which is another embodiment of delivering a catalyst to the hydrogen peroxide solution compared to motor 60 described previously. FIG. 11D shows contact lens cleaning system 600 following removal of cover 50 and reservoir 110 to expose the underlying structures of the system. Features specific to contact lens cleaning system 600 include a spring 112-actuated, tablet-loaded pill helix magazine 108, pill revolver 104 (FIG.

11H), spring-actuated timer and associated gear 116 (FIG. 11E) and a complex pill slide 117. In operation, timer spring is charged by action of pill revolver 104 gear on timer's gear 116 following movement of handle 106 of pill revolver in one direction. After a predetermined time [post-disinfection], the hole of the pill revolver 104 coincides with the proximal, internal opening 119 of the helix system and opening of the pill slide outlet 118 to allow a the spring-pushed tablet to leave the helix magazine 108 and drop, via pill slide 117 and pill slide outlet 118, into the sealed contact lens side of reservoir 110 to initiate neutralization.

FIGS. 12A through 12D are simplified schematic, tridimensional illustrations showing elements, specific parts and possible example details and potential operation in accordance with one or more embodiments of the present disclosure. FIGS. 12A through 12D show contact lens cleaning system 700. Contact lens cleaning system 700 comprises reservoir 110 having two separate compartments: a lens assembly compartment 156 and a tablet-feed compartment 154. Cleaning system 700 includes motor 60B which is another embodiment of motor 60A and 60 used to deliver a catalyst to the hydrogen peroxide solution. The walls compartment 154 are equipped with a built-in tablet-strip track 132 having an external, feeding end 134 and an internal, loading end 136. Hydrogen peroxide neutralization occurs by use of catalase-containing tablets. In operation, strips of aluminum-packaged catalase tablets are fed into track 132 through external feed 134. Post-disinfection, a time-dependent, spring actuated grip-punch assembly 146, by turning handle 144, rotates to grip and advance the tablet-strip along track 132 in front of loading end 136 where a tablet punch 168 to press on the aluminum blister to release the catalase tablet through the pill feed 182 into lens compartment 156 through pill outlet 184.

In one or more embodiments of the present disclosure, the contact lens cleaning systems may have a magnet body that is connected to a flexible, serrated belt, which engages with a motor drive gear. In operation, the motor drive gear rotates to drive the serrated belt down the lumen of the vertical shaft to start neutralization or up at the end of neutralization.

In another embodiments, the solid magnet body may be attached to the distal end of a flexible, yet strong, thin strip or string, which is connected, at its proximal end, to a horizontal motor shaft. At pre-operation and disinfection phases, the strip is coiled/rolled on the motor shaft and the disc is in its up position. Rotation of the motor shaft in one direction uncoils/unrolls the strip or string to push the magnet body downward along the lumen of the vertical shaft, thus downing the iron-embedded, platinum-coated disc into the hydrogen peroxide solution to begin neutralization. At the end of the neutralization phase, the motor counter-rotates to coil/roll the strip or string on its shaft, thus shortening the strip or string, and pulling the magnet body upward (inside the lumen of the vertical shaft) and the iron-embedded, platinum-coated disc upward (outside the lumen of the vertical shaft) and out of the neutralized solution.

Another objective of the present invention is to address the potential surface bio-contamination of contact lens containers and concomitant deposition of biofilm—a thin layer of microorganisms adhering to the surface together with the polymers that they secrete. To this end, components of contact lens container of all embodiments of the present invention may be embedded or surface-coated with effective anti-bacterial agents so that they can self-decontaminate after a bio-contamination event—even an unrecognized one.

Antimicrobials which may be used for said application include, but are not limited to, silver, copper, zinc, titanium, silicon, ammonium, aluminum; their derivatives and combination thereof. By way of example, one may use the metal silver, considered to be the least cytotoxic and most potent agent against bacteria, along with copper, which has a strong antifungal effect—creating a synergistic outcome with respect to practical effectiveness.

Although the present disclosure has been described in detail with reference to particular arrangements and configurations, these example configurations and arrangements may be changed significantly without departing from the scope of the present disclosure. Moreover, the present disclosure is equally applicable to various technologies, aside from those disclosed herein, as these have only been offered for purposes of discussion.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

What is claimed is:

1. An automated two-step cleaning system for the disinfection of contact lenses, the system comprising:
a single reservoir for holding a cleaning solution, said reservoir having a lens side and a disc side;
a complex base comprising a lens segment, a disc segment and a bridge segment, wherein the lens segment is vertically aligned with the lens side of the reservoir, wherein the disc segment is vertically aligned with the disc side of the reservoir, and wherein the bridge segment connects the lens segment with the disc segment;
the complex base being coupled to the reservoir to insure a hermetically closed reservoir environment; and
a lens holder assembly configured to locate and releasably couple lenses within the reservoir, the lens holder being coupled to the lens segment of the complex base;
wherein the disc segment houses a mechanism chamber having a drive mechanism configured to automatically introduce a catalyst into the cleaning solution after a predetermined disinfection time and to remove the catalyst from the cleaning solution after a predetermined neutralization time while the cleaning solution remains in the reservoir
wherein the catalyst is solid and reusable.

2. The cleaning system of claim 1, further comprising:
a locking system configured to selectively prevent the lens holder assembly from being removed from the reservoir during an unsafe condition.

3. The cleaning system of claim 2, wherein the locking system is selected from the group consisting of a mechanical type system and an electrical type system.

4. The cleaning system of claim 2, wherein the locking system is configured to be overridden by a user.

5. The cleaning system of claim 1, wherein the drive mechanism also activates and deactivates a locking system to prevent removal of the lens holder from the reservoir.

6. The cleaning system of claim 1, further comprising:
a user interface configured to provide user feedback regarding the phases of operation of the cleaning system, the user interface being coupled to the mechanism chamber in the disc segment.

7. The cleaning system of claim 1, further comprising:
a concentrate dispensing system configured to create a suitable storage solution for the lenses following neutralization of the cleaning solution.

8. The cleaning system of claim 7, wherein the concentrate dispensing system includes an internal reservoir for holding concentrated storage solution, the internal reservoir located within the reservoir.

9. The cleaning system of claim 7, wherein the concentrate dispensing system includes a canister for holding cleaning solution or concentrated storage solution, the canister in operable communication with the reservoir.

10. A method of cleaning contact lenses in an automated two-step cleaning system, comprising:
   inserting contact lenses into a lens holder assembly;
   coupling the lens holder assembly to a lens segment of a complex base configured to seal a reservoir to ensure a hermetically closed reservoir environment;
   filling the reservoir with cleaning solution to disinfect the contact lenses; and
   automatically introducing a catalyst into the cleaning solution after a predetermined disinfection time, with a mechanical drive mechanism, the catalyst being operably associated with a disc segment of the complex base; and
   automatically removing the catalyst from the cleaning solution after a predetermined neutralization time while the cleaning solution remains in the reservoir,
   wherein the catalyst is solid and reusable.

11. The method of claim 10, further comprising:
   locking the lens holder assembly to the complex base to prevent removal of the lens holder assembly during an unsafe condition.

12. The method of claim 11, wherein the locking is by a locking system selected from the group consisting of a mechanical type system and an electrical type system.

13. The method of claim 12, wherein the locking system is configured to be overridden by a user.

14. The method of claim 10, further comprising:
   activating a drive mechanism to automatically activate and selectively control the cleaning system, the drive mechanism being coupled to a mechanism chamber in the disc segment.

15. The method of claim 14, wherein the drive mechanism is configured to automatically fill the reservoir with the cleaning solution.

16. The method of claim 10, further comprising:
   receiving feedback from the cleaning system regarding the phases of operation of the cleaning system through a user interface.

17. The method of claim 10, further comprising:
   introducing an amount of concentrated storage solution to the neutralized cleaning solution to convert the neutralized cleaning solution into a storage solution.

18. The method of claim 10, further comprising:
   coating components of the cleaning system with antibacterial agents to prevent microbial growth on a surface of the cleaning system.

19. The method of claim 14, wherein the drive mechanism introduces a volume of concentrate solution into the reservoir to convert the neutralized cleaning solution into a storage solution.

* * * * *